US 012402935B2

(12) United States Patent
Legaspi et al.

(10) Patent No.: US 12,402,935 B2
(45) Date of Patent: Sep. 2, 2025

(54) APPARATUS AND METHOD FOR ELECTROSURGERY

(71) Applicant: OLYMPUS MEDICAL SYSTEMS CORP., Tokyo (JP)

(72) Inventors: Danilo Legaspi, Hachioji (JP); Tsuyoshi Hayashida, Hachioji (JP); Yoshitaka Honda, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 920 days.

(21) Appl. No.: 17/558,339

(22) Filed: Dec. 21, 2021

(65) Prior Publication Data

US 2022/0265341 A1   Aug. 25, 2022

Related U.S. Application Data

(60) Provisional application No. 63/151,969, filed on Feb. 22, 2021.

(51) Int. Cl.
*A61B 18/14* (2006.01)
*A61B 18/00* (2006.01)

(52) U.S. Cl.
CPC .. *A61B 18/1442* (2013.01); *A61B 2018/0063* (2013.01); *A61B 2018/00666* (2013.01);
(Continued)

(58) Field of Classification Search
CPC ........... A61B 2018/00666; A61B 2018/00755; A61B 2018/00875; A61B 2018/0063; A61B 18/1442; A61B 18/1445
See application file for complete search history.

(56) References Cited

U.S. PATENT DOCUMENTS

2011/0238056 A1   9/2011   Koss et al.
2012/0016359 A1*  1/2012   Podhajsky ......... A61B 18/1233
                                                 606/34
(Continued)

FOREIGN PATENT DOCUMENTS

CN   102834069 A   12/2012
CN   107106233 A   8/2017
CN   107847263 A   3/2018

OTHER PUBLICATIONS

Office Action dated Apr. 19, 2025, issued in corresponding Chinese Patent Application No. 202210128453.7.

*Primary Examiner* — Sean W Collins
(74) *Attorney, Agent, or Firm* — Morgan, Lewis & Bockius LLP

(57) ABSTRACT

Method, device and treatment system for sealing living tissue using high frequency electrical energy provided to the living tissue by an end effector of a treatment instrument applies N cycles (N=natural number from 1 to 5, inclusive) of electrical energy to the living tissue by increasing, in each cycle, an amount of the high frequency electrical energy provided to the living tissue until the impedance of the living tissue increases to an impedance threshold value for that cycle, after which the amount of high frequency electrical energy is decreased to decrease the impedance of the living tissue by a predetermined value. The cycle repeats, with each subsequent cycle having an impedance threshold value greater than in the prior cycle, and the cycles stop when an N+1-th impedance reaches a impedance stop value. Initial values of impedance can be used to determine parameters of the cycles.

18 Claims, 6 Drawing Sheets

(52) U.S. Cl.
CPC ............... *A61B 2018/00702* (2013.01); *A61B 2018/00726* (2013.01); *A61B 2018/00755* (2013.01); *A61B 2018/00875* (2013.01)

(56) References Cited

U.S. PATENT DOCUMENTS

| | | | |
|---|---|---|---|
| 2013/0338656 A1* | 12/2013 | Irisawa | A61B 18/1206 607/98 |
| 2017/0000542 A1 | 1/2017 | Yates et al. | |
| 2017/0303988 A1 | 10/2017 | Hayashida et al. | |

* cited by examiner

| Vessel Size | Minimum number of cycles; Peak Power |
|---|---|
| Size 1 | 2 cycles; peak power less than P1 |
| Size 2 | 3 cycles; peak power in range from P1 to P2 |
| Size 3 | 4 cycles; peak power greater than P2 |

Figure 5A

| Vessel Size (mm) | Minimum number of cycles; Peak Power (W) |
|---|---|
| 0-3 mm | 2 cycles; peak power <60 W |
| 3-5 mm | 3 cycles; 60 W ≤ peak power ≤ 90 W |
| 5-7 mm | 4 cycles; peak power >90 W |

Figure 5B

APPARATUS AND METHOD FOR ELECTROSURGERY

RELATED APPLICATION DATA

This application is based on and claims priority under 35 U.S.C. § 119 to U.S. Provisional Application No. 63/151,969, filed on Feb. 22, 2021, the entire contents of which are incorporated herein by reference.

TECHNICAL FIELD

The systems, devices and methods disclosed herein are directed to electrosurgery and in particular to electrothermal tissue sealing.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

Many medical procedures include sealing a biological tissue, such as a blood vessel. One of the techniques used for sealing blood vessels is called electrothermal sealing. During an electrothermal sealing procedure, a high frequency electric current is applied to the biological tissue to be sealed, such as a blood vessel of a patient. The current results in localized heating of the biological tissue causing the tissue to dehydrate and denature the tissue. As the current is applied, the impedance of the biological tissue initially reduces as the tissue begins to dry. However, as the tissue denatures, impedance of the tissue increases. Consequently, the current across the tissue decreases thereby reducing the rate of heating off the tissue. This decrease in current results in an increase in the time needed to denature the tissue, thereby increasing the time needed for sealing tissue.

While it is possible to increase the current as the impedance of the tissue increases, there is a risk of damaging the tissue by overheating. Moreover, increasing the current as the impedance increases requires increasing the voltage applied across the tissue thereby making the procedure inefficient and slow.

SUMMARY

To address the above-noted issues in electrothermal sealing, an accurate estimation of the impedance of the biological tissue to be sealed becomes an important factor in improving the time needed for sealing the tissue. Additionally, the present inventors observed that the rate of rise in impedance of the tissue can be decreased by allowing the tissue to cool for a short amount of time when the impedance of the tissue reaches a certain threshold. Without wishing to be bound by theory, the shorter cooling period may allow fluids such as blood or physiological saline to return to the dried portion of the biological tissue causing a decrease in impedance. Such decrease in impedance allows for application of higher current. Interestingly, the present inventors observed that the overall time required for sealing a given biological tissue was reduced by allowing the tissue to cool for a short amount of time during the heating cycle. Advantageously, such a procedure provides more uniform denaturation of the living tissue and thus, a better seal.

In one aspect, it would be advantageous to have improved techniques to more accurately ascertain the size of the biological tissue to be treated so as to better adjust the applied output voltage. An accurate determination of the size of the biological tissue is an important factor for improving the sealing time. In a second aspect, it would be advantageous to have an improved sequence for application of applied output voltage that accounted for the rise in impedance during denaturing and which reduces the application times of the high-frequency current and/or avoids application of higher values of output voltage. To thereby reduce the risk of tissue damage during the sealing procedure.

Thus, in an aspect of the present disclosure, a method for sealing a living tissue using high frequency electrical energy provided to the living tissue by an end effector of a treatment instrument is disclosed. The method may include applying an amount of high frequency electrical energy to the living tissue in at least two cycles. The at least two cycles include a N-th cycle and a N+1-th cycle, the N+1-th cycle following the N-th cycle. The N-th cycle includes: increasing an amount of the high frequency electrical energy applied to the living tissue until the impedance of the living tissue reaches an N-th impedance threshold value, and when the impedance of the living tissue reaches the N-th impedance threshold value, decreasing the impedance of the living tissue by decreasing the amount of the high frequency electrical energy applied to the living tissue. The N+1-th cycle includes: increasing the amount of the high frequency electrical energy applied to the living tissue until the impedance of the living tissue reaches an N+1-th impedance threshold value. The N+1-th impedance threshold value is greater than the N-th impedance threshold value.

In some embodiments, the method further comprises, when the impedance of the living tissue reaches the N+1-th impedance threshold value, decreasing the impedance of the living tissue by decreasing the amount of the high frequency electrical energy applied to the living tissue.

In some embodiments, the N+1-th impedance threshold value is an N+1-th impedance stop value, and the method further comprises: when the impedance of the living tissue reaches an N+1-th impedance stop value, stopping the application of high frequency electrical energy to the living tissue.

In some embodiments, N is a natural number and a value of N is equal to or greater than 1 to equal to or less than 5.

In some embodiments, N=1 and the N-th cycle of the method further comprises: determining an initial impedance value by applying a constant power to the end effector for a predetermined period of time while the end effector is in contact with the living tissue. Determining the initial impedance value occurs prior to increasing the amount of the high frequency electrical energy applied to the living tissue in the N-th cycle.

In some embodiments, a rate of increase of the high frequency electrical energy applied to the living tissue in the N-th cycle is determined based on the initial impedance value.

In some embodiments, the method further comprises determining the value of N based on the value of the initial impedance value.

In some embodiments, the method further comprises determining a size parameter associated with the living tissue based on the initial impedance value.

In some embodiments, the method further comprises determining the value of N based on the size parameter.

In some embodiments, the method further comprises estimating the N-th impedance threshold value based on the size parameter.

In some embodiments, a rate of increase of the high frequency electrical energy applied to the living tissue in the N+1-th cycle is different from the rate of increase of the high frequency electrical energy provided to the living tissue in the N-th cycle.

In some embodiments, the N+1-th cycle of the method further comprises: determining an N+1-th initial impedance value by applying a constant power to the end effector for a predetermined period of time while the end effector is in contact with the living tissue. Determining the N+1-th initial impedance value occurs prior to increasing the amount of the high frequency electrical energy applied to the living tissue in the N+1-th cycle.

In some embodiments, a rate of increase of the high frequency electrical energy applied to the living tissue in the N+1-th cycle is determined based on the N+1-th initial impedance value.

In some embodiments, the rate of increase of the high frequency electrical energy applied to the living tissue in the N+1-th cycle is different from a rate of increase of the high frequency electrical energy provided to the living tissue in the N-th cycle.

In another aspect of the present disclosure, a device for sealing a living tissue may include an energy source configured to generate high frequency electrical energy and an end effector operably connected to the energy source and configured to provide the high frequency electrical energy to the living tissue. A controller is operably connected to the energy source and the end effector, and is configured, in operation, to apply an amount of the high frequency electrical energy to the living tissue in at least two cycles. The at least two cycles include a N-th cycle and a N+1-th cycle, the N+1-th cycle following the N-th cycle. In the N-th cycle, the controller is further configured, in operation, to: increase an amount of the high frequency electrical energy applied to the living tissue until the impedance of the living tissue reaches an N-th impedance threshold value, and when the impedance of the living tissue reaches the N-th impedance threshold value, decrease the impedance of the living tissue by decreasing the amount of the high frequency electrical energy applied to the living tissue. In the N+1-th cycle, the controller is further configured, in operation, to: increase the amount of the high frequency electrical energy applied to the living tissue until the impedance of the living tissue reaches an N+1-th impedance threshold value. The N+1-th impedance threshold value is greater than the N-th impedance threshold value.

In some embodiments, wherein, in the N+1-th cycle, the controller is further configured, in operation, to decrease the impedance of the living tissue by decreasing the amount of the high frequency electrical energy applied to the living tissue when the impedance of the living tissue reaches the N+1-th impedance threshold value.

In some embodiments, the N+1-th impedance threshold value is an N+1-th impedance stop value. In the N+1-th cycle, the controller is further configured, in operation, to stop the application of high frequency electrical energy to the living tissue when the impedance of the living tissue reaches an N+1-th impedance stop value.

In some embodiments, N is a natural number and a value of N is equal to or greater than 1 to equal to or less than 5.

In some embodiments, N=1, and in the N-th cycle, the controller is further configured, in operation, to determine an initial impedance value by applying a constant power to the end effector for a predetermined period of time while the end effector is in contact with the living tissue. Determining the initial impedance value occurs prior to increasing the amount of the high frequency electrical energy applied to the living tissue in the N-th cycle.

In some embodiments, a rate of increase of the high frequency electrical energy applied to the living tissue in the N-th cycle is determined based on the initial impedance value.

In some embodiments, the controller is further configured, in operation, to determine the value of N based on the value of the initial impedance value.

In some embodiments, the controller is further configured, in operation, to determine a size parameter associated with the living tissue based on the initial impedance value.

In some embodiments, the controller is further configured, in operation, to determine the value of N based on the size parameter.

In some embodiments, the controller is further configured, in operation, to estimate the N-th impedance threshold value based on the size parameter.

In some embodiments, a rate of increase of the high frequency electrical energy applied to the living tissue in the N+1-th cycle is different from the rate of increase of the high frequency electrical energy provided to the living tissue in the N-th cycle.

In some embodiments, in the N-th cycle, the controller is further configured, in operation, to determine an N+1-th initial impedance value by applying a constant power to the end effector for a predetermined period of time while the end effector is in contact with the living tissue. The N+1-th initial impedance value is determined prior to increasing the amount of the high frequency electrical energy applied to the living tissue in the N+1-th cycle.

In some embodiments, a rate of increase of the high frequency electrical energy applied to the living tissue in the N+1-th cycle is determined based on the N+1-th initial impedance value.

In some embodiments, the rate of increase of the high frequency electrical energy applied to the living tissue in the N+1-th cycle is different from a rate of increase of the high frequency electrical energy provided to the living tissue in the N-th cycle.

In yet another aspect of the present disclosure, a treatment system may include any device disclosed herein.

Additional features and advantages will be set forth in the description that follows, and in part will be apparent from the description, or may be learned by practice of the invention. The objectives and other advantages of the disclosed input device will be realized and attained by the structure particularly pointed out in the written description and claims thereof as well as the appended drawings.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIGS. 5A and 5B illustrate examples of the number of cycles to be used during the sealing a blood vessel and the peak power input to the blood vessel, in accordance with some embodiments.

Figure 1:
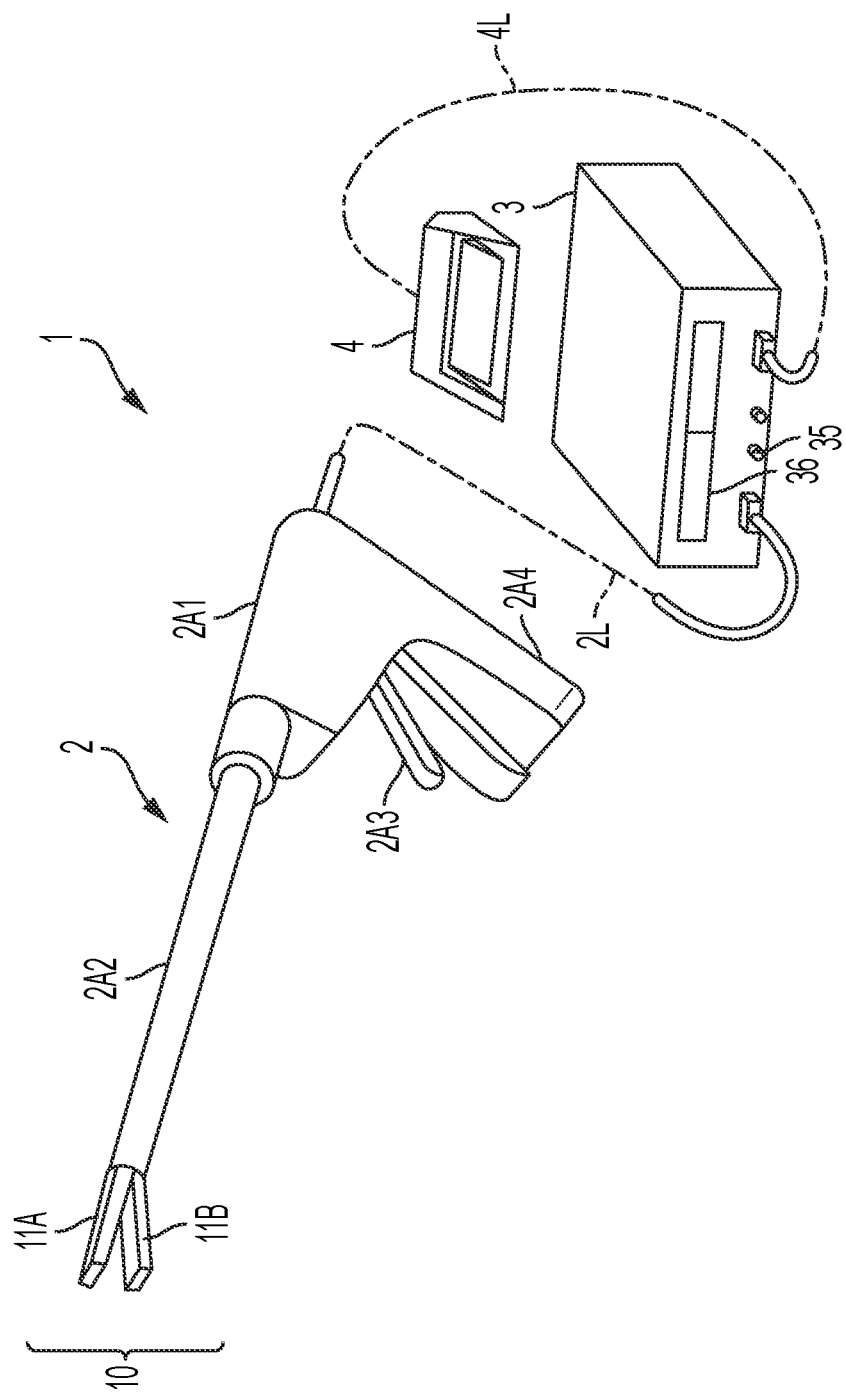
FIG. 1 shows a schematic of a medical device for heating a tissue, in accordance with some embodiments.

Throughout all of the drawings, dimensions of respective constituent elements are appropriately adjusted for clarity. For ease of viewing, in some instances only some of the named features in the figures are labeled with reference numerals.

DETAILED DESCRIPTION

Embodiments of electrothermal sealing methods for sealing a biological tissue of a patient using high frequency electrical energy (and devices and treatment systems operatively configured to include the electrothermal sealing methods) apply N cycles (N=natural number from 1 to 5, inclusive) of electrical energy to the living tissue by increasing, in each cycle, an amount of the high frequency electrical energy provided to the living tissue until the impedance of the living tissue increases to an impedance threshold value for that cycle, after which the amount of high frequency electrical energy is decreased to decrease the impedance of the living tissue by a predetermined value. The cycle repeats, with each subsequent cycle having an impedance threshold value greater than in the prior cycle, and the cycles stop when an N+1-th impedance reaches a impedance stop value. Initial values of impedance can be used to determine parameters of the tissue that are then used to adjust parameters of the cycles, such as one or more of number of cycles, time of each cycle, initial power settings for each cycle, rates of increase of the power with each cycle, impedance threshold value for each cycle, and an impedance stop value.

In an aspect of the present disclosure, the method for sealing a living tissue of a patient using high frequency electrical energy provided to the living tissue by an end effector of a treatment instrument is disclosed. The method may include cycling the electrical energy supplied to the living tissue by increasing, in an N-th cycle, an amount of the high frequency electrical energy provided to the living tissue until the impedance of the living tissue increases to an N-th impedance threshold value. The amount of high frequency electrical energy provided to the living tissue is decreased when the impedance of the living tissue reaches the N-th impedance threshold value so as to enable a decrease in the impedance of the living tissue by a predetermined value. The high frequency electrical energy provided to the living tissue is stopped when, in an N+1-th cycle, an impedance stop value is reached. The N+1-th impedance threshold value is greater than the N-th impedance threshold value. N is a natural number and, in exemplary embodiments, has a value equal to or greater than 1 to equal to or less than 5.

In another aspect of the present disclosure, the method for sealing a living tissue of a patient using high frequency electrical energy provided to the living tissue by an end effector of a treatment instrument is disclosed. The method may include cycling the electrical energy supplied to the living tissue by increasing, in an N-th cycle, an amount of the high frequency electrical energy provided to the living tissue until the impedance of the living tissue increases to an N-th threshold. The amount of high frequency electrical energy provided to the living tissue is decreased when the impedance of the living tissue reaches the N-th threshold for a predetermined period of time. The high frequency electrical energy provided to the living tissue is stopped when an N+1-th threshold reaches a stop threshold. N is a natural number, and the N+1-th threshold is greater than the N-th threshold.

High frequency, as used herein, refers to a frequency in a range from about 100 kHz to about 5 MHz. Thus, depending on the specific application, a device may supply electrical energy to the living tissue by applying a voltage at a frequency of, e.g., 100 kHz, 150 kHz, 200 kHz, 250 kHz, 300 kHz, 350 kHz, 400 kHz, 450 kHz, 500 kHz, 600 kHz, 700 kHz, 800 kHz, 900 kHz, 1000 kHz, 1500 kHz, 2000 kHz, 2500 kHz, 3000 kHz, 3500 kHz, 4000 kHz, 4500 kHz, 5000 kHz, or any frequency between any two of these frequencies.

The term "patient," as used herein, comprises any and all organisms and includes the term "subject." A patient can be a human or an animal.

Medical Device for Heating Tissue

FIG. 1 shows a schematic of a medical device for heating a tissue, in accordance with an embodiment of the present disclosure. As shown in FIG. 1, the medical device 1 for sealing a tissue is provided with an instrument 2, a controller 3 having a processor, and an actuation switch 4. The instrument 2 may be, for example, a clamp used for grasping a biological tissue during an electrosurgical procedure.

The treatment instrument 2 has a grip 2A1, a shaft 2A2, and a treatment section constituted by an end-effector 10 such as, for example, an openable or pivoting pair of grasping sections (including a first grasping section 11A and a second grasping section 11B) for grasping living tissue (LT) to perform treatment. The grasping sections as whole are also referred to herein as the "treatment portion" or the "treatment section" of the medical instrument. Note that, hereinafter, at time of mentioning each of components having a same function and having reference numerals with A and B attached to ends of the reference numerals, respectively, the symbol A or B may be omitted. For example, each of the first grasping section 11A and the second grasping section 11B may be referred to as the grasping section. In some embodiments, the actuation switch may be provided at the grip 2A1.

The grip 2A1 is connected to the controller 3 via a cable 2L. The grip 2A1 has an opening/closing actuator 2A3, such as a trigger, for a surgeon to operate opening and closing of the treatment section in such a shape that the surgeon can easily clasp the tissue. The opening/closing actuator 2A3 is arranged at one end of the grip 2A1 and is integrated with the treatment section to transmit operation of the opening/closing actuator 2A3 to the treatment section. On the other side of the grip 2A1, a grasping portion 2A4 is provided for a clinician to grasp when operating the instrument 2.

Figure 2:
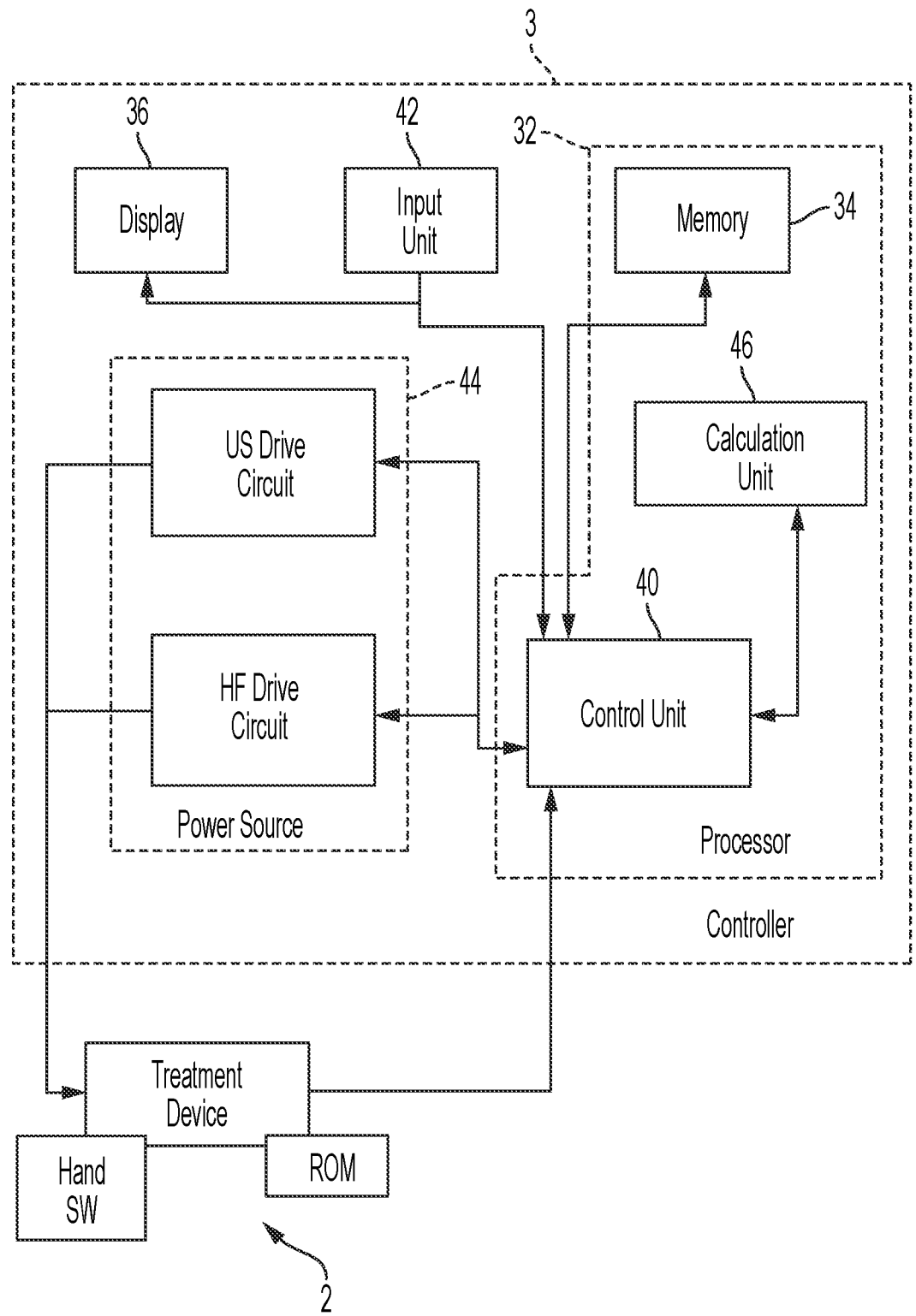
FIG. 2 shows a schematic of a controller in accordance with embodiments.

FIG. 2 shows a schematic of a controller in accordance with an embodiment of the present disclosure. The controller 3 may include a processor 32, a display 36, an input unit 42, and a power source 44.

The processor 32 may include a memory 34, a calculation unit 46 and a control unit 40. The calculation unit 46 and the control unit 40 are formed of an integrated circuit including a CPU (Central Processing Unit), an ASIC (Application Specific Integrated Circuit) or an FPGA (Field Programmable Gate Array). The calculation unit 46 and the control unit 40 may be formed of a single integrated circuit, or may be formed of a plurality of integrated circuits.

In some embodiments, various parameters used for determining an impedance of the living tissue such as, for example, the size of the tissue, the type of the tissue, or any other factors that determine the impedance of the tissue may be stored in memory 34, e.g., in a look-up table stored in the memory 34. The look-up table may include the values of the corresponding parameters for different treatment portions. For example, the look-up table may include the parameters for muscle tissue, adipose tissue, blood vessels, intestinal wall, or other tissue types. The calculation unit 46 is configured to compute the impedance at the beginning of or during a given heating cycle as well as other parameters that are needed for computing the impedance. The control unit 40 is configured to control the power source 44 and the display 36 based on the commands provided by the processor 32 using the parameters computed by the calculation unit 46.

The display 36 that displays treatment conditions and the like, and a setting operation section 35 that permits the surgeon to set the treatment conditions and the like, are on a front panel of the controller 3. In some embodiments, the controller 3 may be connected to a switch 4 via a cable 4L. The switch 4 may be used by the clinician performing the procedure for controlling power applied to the instrument, for example, between sealing two different vessels.

In some embodiments, the power source 44 is operatively coupled to a processor 32 which controls the application of power to the instrument 2 via the power source 44 so as to appropriately cycle the power applied to the living tissue during the sealing procedure.

To control the power input to the instrument 2, the processor 32 may determine an impedance of the living tissue during the procedure and determine whether the impedance has reached a certain threshold for a given cycle. In addition, the processor 32 may determine the number of cycles for which to increase the power input to the instrument for appropriately sealing the living tissue.

In some embodiments, the number of cycles for which to increase the power input to the instrument 2 for sealing the living tissue is determined based on an initial impedance $Z_0$ of the tissue determined before the first cycle is initiated. For example, when the clinician initiates the procedure for sealing the living tissue, the processor 32 may control the power source 44 to apply a constant power for determining the initial impedance $Z_0$.

In some embodiments, the processor 32 is configured to determine various parameters associated with the living tissue based on a measured impedance of the living tissue. For example, the processor 32 may determine a size of the living tissue based on the initial impedance $Z_0$. For instance, in case of blood vessels, there is a direct correlation between the size (e.g., diameter) of the vessel and the impedance of the blood vessel. Thus, the processor 32 determines the size of the blood vessel based on the initial impedance $Z_0$.

An initial impedance of the tissue may thus, be an indicator of the size of the tissue, and parameters such as the number of cycles needed for sealing the tissue of that size, and the threshold impedances at various time points at which the electrical energy provided to the tissue is to be increased or decreased. However, depending on the particular circumstances, the initial impedance of the tissue may not be an accurate indicator of the size. For example, if there is excessive amount of external fluid surrounding the tissue the initial impedance may be lower than a typical tissue of that size. Thus, estimating the state of the tissue during the procedure may be helpful in improving the efficiency of the procedure, as well as improving patient safety by avoiding damage to the tissue during the procedure.

Accordingly, in some embodiments, the processor 32 may also be configured to determine the state of the living tissue based on the impedance of the tissue at various time points during the procedure, for example, to determine an end point of the procedure. Additionally or alternatively, the state of the living tissue determined during the procedure may be used to determine when and/or by how much the electrical energy being supplied to the tissue should be increased or decreased. The state of the living tissue, as used to herein, may refer to an amount of moisture in the tissue (i.e., dryness of the tissue), or the state of denaturation of the tissue. In embodiments in which impedance is determined during various time points during the procedure, such impedance may be an initial impedance $Z_0$ of the tissue before each cycle is initiated $Z_{0,N}$ or may be impedance values that are determined at various predetermined times during each cycle, for example at one or more of fractional times of the estimated cycle time, such as one or more of intervals of 0.1, 0.2, 0.25, 0.3 0.33, 0.4, 0.5, 0.6, 0.67, 0.7, 0.75, 0.8, and 0.9 of the individual cycle time $T_{c,N}$. For example, in an embodiment, a low constant power is applied to the tissue at the beginning of the phase for a predetermined time, such as about 250 ms, and an average of the tissue impedance at an end period of the predetermined time (which is typically during the low constant power output period of the predetermined time), such as from about 230 ms to about 250 ms for a 250 ms predetermined time, is considered as the initial impedance.

As discussed herein, the moisture in the tissue may decrease the impedance while denaturation of the tissue may increase the impedance. Thus, a measured impedance of the tissue may indicate the state of the living tissue depending on the time point at which the impedance is measured during the procedure. The processor 32 may thus, determine whether an end point of the procedure has reached or if the cycling of the electrical energy being supplied to the tissue should be continued. For example, the processor 32 may determine that the procedure should be stopped if the impedance of the tissue reaches a certain stop threshold $Z_{stop}$. On the other hand, in case the processor 32 determines that the cycling should be continued, the processor 32 may further determine the number of cycles for which the cycling should be continued based on the current state of the living tissue.

During the cycling of the electrical energy input to the living tissue, the processor 32 may initially increase the electrical energy input to the living tissue until the impedance of the tissue increases to a given threshold determined based on the number of cycles completed. For example, during an N-th cycle, the amount of electrical energy input to the tissue is increased till the impedance of the tissue increases to an N-th impedance threshold value.

Once the processor 32 determines that impedance of the tissue reaches the given threshold, e.g., an N-th impedance threshold value $Z_N$, the amount of electrical energy supplied to the tissue is decreased for a certain amount of time. Without wishing to be bound by theory, this temporary decrease in the electrical energy supplied to the tissue allows moisture to return to the tissue, thereby decreasing the impedance of the tissue. Once the impedance of the tissue decreases by a certain value, the processor 32 initiates the next cycle, i.e., an N+1-th cycle, and increases the electrical energy supplied to the tissue so as to increase the impedance of the tissue to an N+1-th impedance threshold value $Z_{N+1}$ which is greater than $Z_N$. The cycling is stopped when $Z_{N+1}$ reaches a impedance stop value $Z_{Stop}$ indicating that the sealing process is complete.

Figure 3:
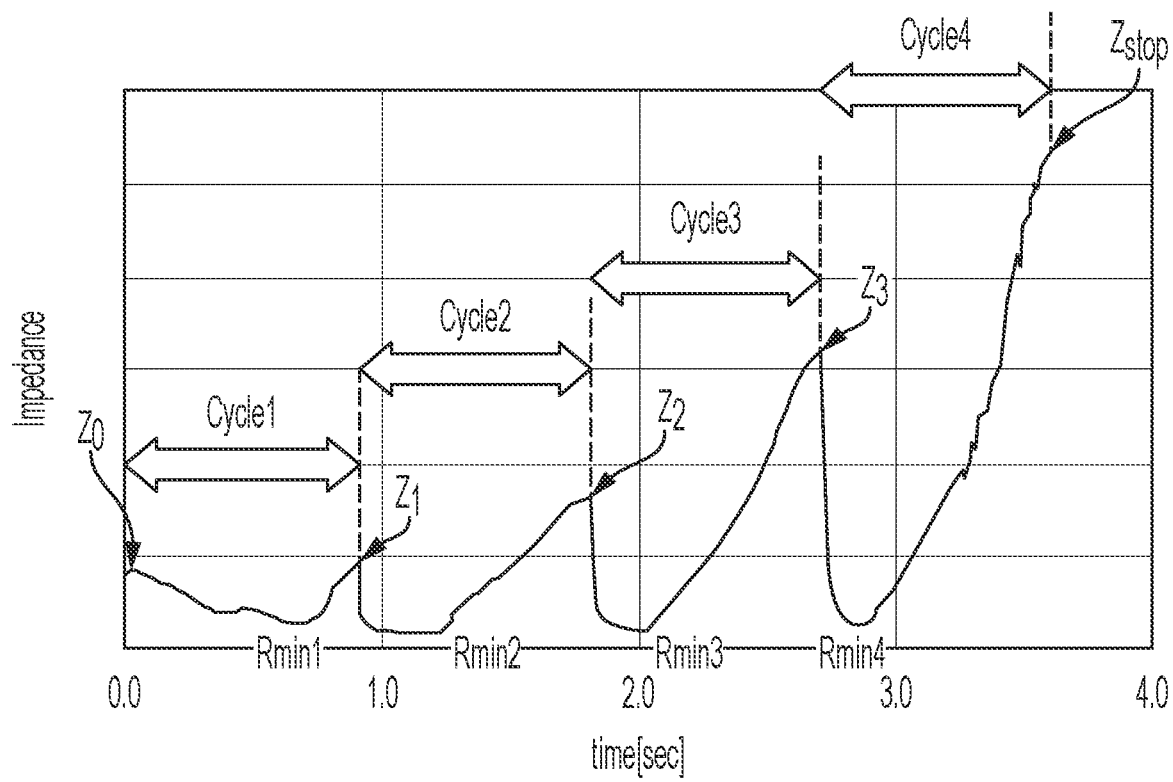
FIG. 3 illustrates an example of the change in impedance of the tissue caused by the cycling of electrical energy provided to the tissue for four cycles in accordance with some embodiments.

FIG. 3 illustrates an example of the change in impedance of the tissue caused by the cycling of electrical energy provided to the tissue for four cycles in accordance with an embodiment of the present disclosure. As shown in FIG. 3, after determining the initial impedance of the tissue $Z_0$ by applying a constant power, e.g., a low power, across the tissue, the voltage is increased at a constant rate in the subsequent phase of the cycle and the tissue impedance initially decreases to $R_{min1}$ and then increases to a first impedance threshold value $Z_1$ at the end of the Cycle 1. A low constant power is then applied to the tissue at the beginning of Cycle 2 for a predetermined period of time, during which the impedance of the tissue decreases to $R_{min2}$. The voltage is then increased again at a constant rate causing the impedance of the tissue to increase to a second impedance threshold value $Z_2$ at the end of the second cycle. During the third cycle, a low constant power is again applied to the tissue for a predetermined period of time, during which the impedance of the tissue to decreases to $R_{min3}$. When the impedance reaches $R_{min3}$, the voltage is again increased thereby increasing the impedance of the tissue to a third impedance threshold value $Z_3$ at the end of the third cycle. During the fourth cycle, a low constant power is again applied to the tissue for a predetermined period of time, during which the impedance of the tissue decreases to $R_{min4}$, and the voltage is again increased thereby increasing the impedance of the tissue to a fourth impedance threshold value at the end of the fourth cycle, which in this example is an impedance stop value $Z_{stop}$. Upon determination that the impedance of the tissue has reached $Z_{stop}$, the supply of electrical energy to the tissue is stopped to complete the procedure.

In the embodiment illustrated in FIG. 3, the cycle begins at a higher impedance, and during the cycle, the impedance first decreases and then increases to a certain threshold. In some embodiments, the processor 32 may define the beginning of a cycle at a lower impedance, and during the cycle, the impedance first increases and then decreases. Thus, those of skill in the art will appreciate that the beginning and end of cycles may be arbitrarily defined so long as the cycles can be reproducibly defined. However, defining the beginning of the cycle at a transition point between increasing or decreasing the impedance (i.e., increasing or decreasing voltage applied across the tissue) are the more logical choices.

The amount by which the impedance is allowed to be decreased, i.e., $(Z_N - R_{minN+1})$ during a given cycle may be pre-determined based, for example, on the cycle number, the size of the tissue, the initial impedance of the tissue, or some combination thereof. Additionally or alternatively, the value to which the impedance is allowed to be decreased (i.e., $R_{minN+1}$) during a given cycle may be pre-determined based on the same or different combination of parameters. Further, the value to which the impedance is allowed to be decreased during a given cycle (e.g., N+1-th cycle) may be greater than the value to which the impedance is allowed to be decreased during an immediately preceding cycle (e.g., N-th cycle).

In other words, in each subsequent cycle, the processor 32 cycles the electrical energy that is supplied to the tissue such that the maximum impedance during the cycle is greater than the maximum impedance during the immediately preceding cycle, and the minimum impedance during the cycle is greater than the minimum impedance during the immediately preceding cycle, e.g., $Z_{N+1} > Z_N$, and $R_{minN+1} > R_{minN}$.

In example embodiments, the impedance threshold value for each cycle is determined by adding a predetermined value to the minimum value from the prior cycle. This predetermined value can be incremented by a constant value for each subsequent cycle. Example constant values for the increment are in the range of 20Ω to 100Ω, such as 20Ω, 30Ω, 40Ω, 50Ω, 60Ω, 70Ω, 80Ω or any value in between these values. In one specific example the constant value for the increment is 50Ω. Thus, as an example, if the Nth cycle had a minimum impedance ($R_{minN}$), then the impedance threshold value for the N+1-th cycle would be ($R_{minN}$+50Ω). Continuing to the next cycle, if the N+1-th cycle had a minimum impedance ($R_{minN+1}$), then the impedance threshold value for the next cycle, the N+2-th cycle, would be ($R_{minN+1}$+100Ω). Additional cycles would have the impedance threshold value increased by additional +50Ω increments, e.g., +150Ω, +200Ω, etc., until the last cycle and the procedure stops.

In some embodiments, the processor 32, upon determining the initial impedance $Z_0$ may determine one or more of (a) the number of cycles, (b) the value to which the impedance of the tissue is allowed to increase during each cycle, (c) the amount of electrical energy supplied to the tissue when the impedance of the tissue is allowed to increase (on a total or per cycle basis or both), (d) the amount of time for which the impedance of the tissue is allowed to increase (on a total or per cycle basis or both), (e) the value to which or by which the impedance of the tissue is allowed to decrease during each cycle, (f) the amount of time for which the electrical energy supplied to the tissue is decreased during each cycle, (g) the value by which the electrical energy supplied to the tissue is decreased during each cycle, (h) the impedance threshold values for each cycle at which the supply of electrical energy to the tissue is decreased, and (i) the impedance stop value for the procedure at which the supply of electrical energy to the tissue is stopped.

In some embodiments, the processor 32 may determine one or more of the parameters (a)-(i) at the beginning of each cycle. Those of skill in the art will appreciate that determination of some of these parameters may be based on the determination of some of the other parameters. For example, determination of (d) may be dependent on the determination of (b) and (c).

Thus, when a clinician initiates the sealing procedure, the processor 32 first determines the initial impedance by applying a predetermined constant power and measuring the current through the living tissue. The processor 32 then provides cycles of electrical energy to the tissue until a measured impedance of the tissue reaches a impedance stop value. The iterative increase is performed based on one or more of the parameters (a)-(i).

In another aspect, the present disclosure relates to a method for sealing a living tissue using high frequency electrical energy that decreases the total amount of time needed to seal the living tissue. For example, in some embodiments, the method includes applying the amount of electrical energy provided to the living tissue in cycles so as, in each cycle, to first increase and then decrease the impedance of the tissue. During each subsequent cycle the impedance of the tissue is allowed to increase to a value more than that from the immediately preceding cycle until the impedance reaches a impedance stop value, when supply of the electrical energy to the tissue is stopped and the sealing process is completed.

Figure 4:
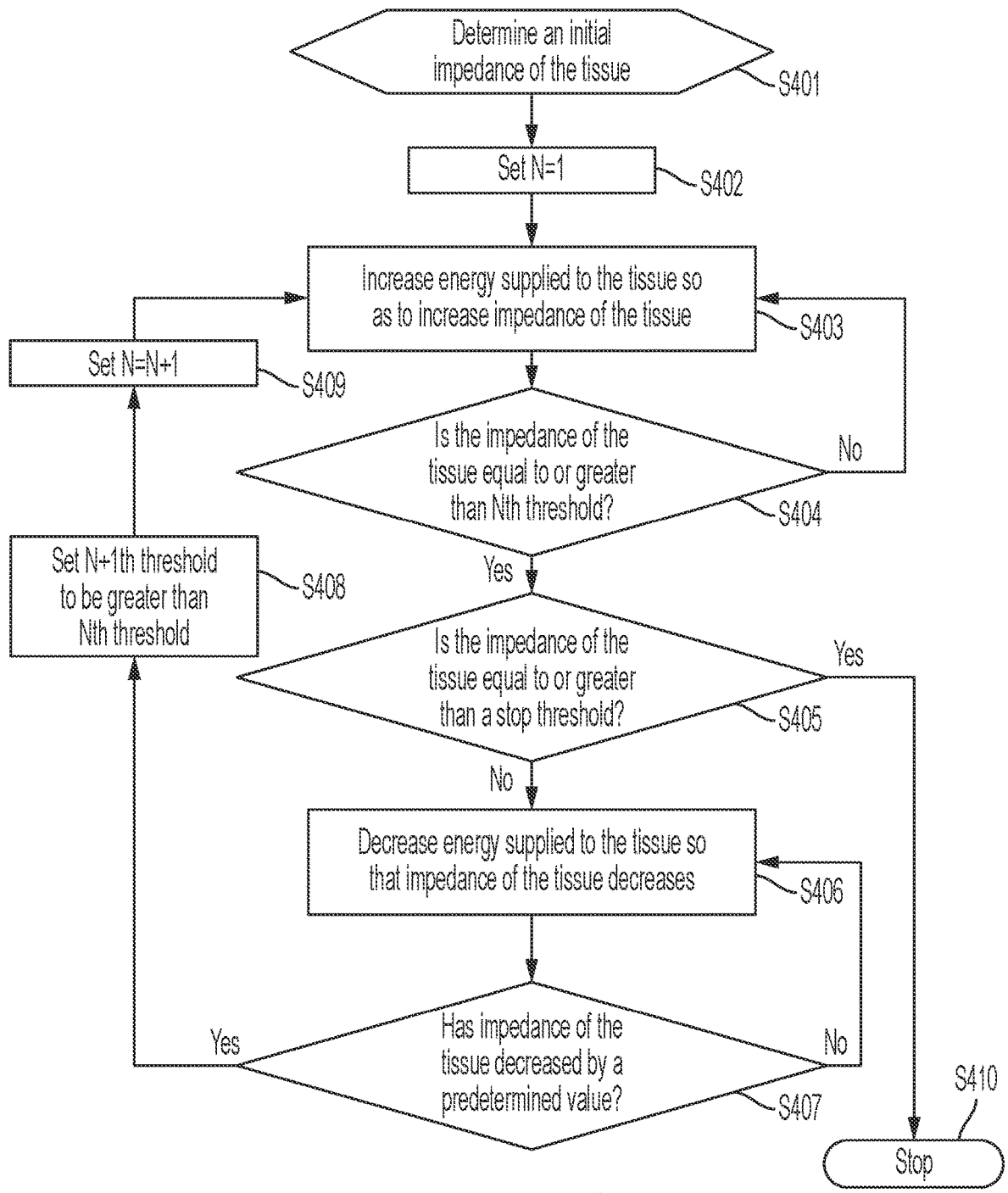
FIG. 4 illustrates a flow chart for a method of sealing a living tissue in accordance with some embodiments.

FIG. 4 illustrates a flow chart for a method of sealing a living tissue in accordance with some embodiments. Referring to FIG. 4, in some embodiments, the method of sealing a living tissue may optionally include, at S401, determining an initial impedance of the tissue. To determine the initial impedance, in some embodiments, a constant power is applied across the tissue for a certain amount of time. The initial impedance of the tissue may then be determined measuring the current flowing through the tissue during that time.

Those of skill in the art recognize that depending on the power being applied and the time for which it is applied, the application of the power across the tissue may result in increasing the impedance of the tissue as the tissue dehydrates. Thus, the value of power and amount of time for which it is applied is selected appropriately to minimize the dehydration of the tissue. For example, in some embodiments, the constant power may be applied for about 10 ms, about 20 ms, about 30 ms, about 40 ms, about 50 ms, about 60 ms, about 70 ms, about 80 ms, about 90 ms, about 100 ms, about 120 ms, about 140 ms, about 160 ms, about 180 ms, about 200 ms, about 250 ms, about 300 ms, about 350 ms, about 400 ms, about 450 ms, about 500 ms, or any period of time between any two of these values. Similarly, the applied power may be 5 W, about 10 W, about 15 W, about 20 W, about 25 W, about 30 W, about 35 W, about 40 W, about 45 W, about 50 W, about 55 W, about 60 W, about 65 W, about 70 W, about 75 W, about 80 W, about 85 W, about 90 W, about 95 W, about 100 W, about 110 W, about 120 W, about 130 W, about 140 W, about 150 W, about 175 W, about 200 W, or any value between any two of these values.

One or more parameters relating to the tissue such as, for example, the size of the tissue, are determined based on the initial impedance of the issue. Additionally, other parameters such as, for example, the number of cycles to be used for sealing, and the peak power that can be used during the sealing process are determined based on the size of the tissue.

FIG. 5A illustrates an example of determination of the number of cycles to be used during sealing of a blood vessel and the peak power input to the blood vessel, in accordance with some embodiments. For example, if the size of the vessel is "Size 1" the sealing process is performed for at least two cycles and peak power of less than P1 is used. If the size of the vessel is "Size 2" (greater than "Size 1"), the sealing process is performed for at least three cycles and peak power in a range from P1 to P2 is used. If the size of the vessel is "Size 3" (greater than "Size 2"), the sealing process is performed for at least four cycles and peak power greater than P2 is used.

FIG. 5B illustrates another example with the number of cycles to be used during sealing of a blood vessel and the peak power input to the blood vessel, in accordance with some embodiments. In this example, the size of the blood vessel (diameter, in mm) and the associated minimum number of cycles and Peak Power Range (in Watts) are given and are based on empirical studies.

Returning to the method of sealing a living tissue graphically illustrated in FIG. 4, the method continues and the cycle counter N is then set to 1 at S402.

Based on these parameters, at S403, in the Nth cycle, the electrical energy supplied to the tissue is increased so as to increase the impedance of the tissue. During S403, the voltage applied across the tissue is increased for a certain amount of time or until the impedance of the tissue reaches an Nth threshold. The rate at which the voltage applied across the tissue is increased may be determined based on one or more parameter such as, for example the size and/or type of the tissue in some embodiments. For instance, depending on the size and/or type of the tissue, a peak voltage to be applied across the tissue may be determined, and the rate of increase of the voltage may then be determined. In some embodiments, the voltage may be increased over a period of time ranging from about 600 ms to about 3000 ms. For example, the voltage may be increased for about 600 ms, about 610 ms, about 620 ms, about 630 ms, about 640 ms, about 650 ms, about 660 ms, about 670 ms, about 680 ms, about 690 ms, about 700 ms, about 720 ms, about 740 ms, about 760 ms, about 780 ms, about 800 ms, about 825 ms, about 850 ms, about 875 ms, about 900 ms, about 950 ms, about 1000 ms, about 1100 ms, about 1200 ms, about 1300 ms, about 1400 ms, about 1500 ms, about 1600 ms, about 1700 ms, about 1800 ms, about 1900 ms, about 2000 ms, about 2200 ms, about 2400 ms, about 2600 ms, about 28000 ms, about 3000 ms, or any amount of time between any two of these values. While those of skill in the art will recognize certain advantages and disadvantages of increasing the voltage over a period that is shorter than 600 ms or greater than 3000 ms, processes in which the voltage is increased over a period of less than 600 ms or greater than 3000 ms are also contemplated within the scope of the present disclosure.

The rate of increase in the high frequency electrical energy applied to the living tissue in the N-th cycle and in the N+1-th cycle may be the same, or the rate of increase in the high frequency electrical energy applied to the living tissue in each cycle may be different. For example, in some embodiments, the rate of increase of the high frequency electrical energy applied to the living tissue in the N-th cycle is determined based on the initial impedance value, and the rate of increase of the high frequency electrical energy applied to the living tissue in the N+1-th cycle is different from the rate of increase of the high frequency electrical energy provided to the living tissue in the N-th cycle. Also for example, the rate of increase of the high frequency electrical energy applied to the living tissue in the N+1-th cycle is determined based on the N+1-th initial impedance value, and the rate of increase of the high frequency electrical energy applied to the living tissue in the N+1-th cycle is different from a rate of increase of the high frequency electrical energy provided to the living tissue in the N-th cycle. Example differences in rate of increases between an N-th cycle and a N+1-th cycle include, but are not limited to, 20 V/s, 22 V/s, 24 V/s, 26 V/s, 28 V/s, 30 V/s, 32 V/s, 34 V/s, 36 V/s, 38 V/s, 40 V/s, 42 V/s, 44 V/s, 46 V/s, 48 V/s, 50 V/s, 52 V/s, 54 V/s, 56 V/s, 58 V/s, 60 V/s, 62 V/s, 64 V/s, 66 V/s, 68 V/s, 70 V/s, or any value between any two of these values, depending on the size of the tissue, such as the vessel. For example, in some embodiments, the rate of voltage increase is about 36 V/s for a small vessel, and about 52 V/s for a large vessel.

At S404, the impedance of the tissue is compared to the Nth threshold. If it is determined that the impedance has not reached the Nth threshold, additional electrical energy may be supplied to the tissue in some embodiments. If it is determined that the impedance of the tissue is greater than or equal to the Nth threshold, the process moves to S405.

At S405, the impedance of the tissue is compared with a stop threshold at which the sealing process is deemed to be complete. If the impedance of the tissue is greater than or equal to the stop threshold, the sealing process jumps to S410, where the power input to the tissue is stopped so as to stop the sealing process.

If the impedance of the tissue at S405 is determined to be less than the stop threshold, the process moves to S406 where the electrical energy supplied to the tissue is decreased so as to allow the impedance of the tissue to decrease.

As discussed elsewhere herein, once the electrical energy supplied to the tissue is decreased, e.g., by decreasing the power input to the tissue (by decreasing the voltage across the tissue), the impedance of the tissue may decrease by, for example, allowing the tissue to rehydrate or by allowing electrolytes to diffuse to the tissue.

At S406, the electrical energy supplied to the tissue is reduced until the impedance of the tissue is decreased by a predetermined value. In some embodiments, the predetermined value may be dependent on the size and/or type of the tissue. In some embodiments, the predetermined value in a given cycle is based on the cycle counter N.

At S407, it is determined whether the impedance of the tissue after decreasing the electrical energy supplied to the tissue has decreased by a predetermined value. If it is determined that the impedance has not decreased by the predetermined value, the electrical energy is further reduced, or in instances where further reduction is not possible, the electrical energy is maintained at the reduced level for a longer duration of time so as to allow the impedance to decrease by the predetermined value.

If it is determined that the impedance has decreased by the predetermined value, at S408, the threshold impedance for the subsequent cycle, i.e., N+1-th threshold, is set to be higher than that of the current cycle (i.e., the Nth cycle). The N+1-th threshold may be set to be greater by a certain predetermined value in some embodiments. The predetermined value by which the N+1-th threshold is greater than the Nth threshold may be based on the size of the tissue and/or the type of the tissue in some embodiments.

The cycle counter is then set, at S409, to N+1 (i.e., N=N+1), after which the process continues at S403.

Figure 6:
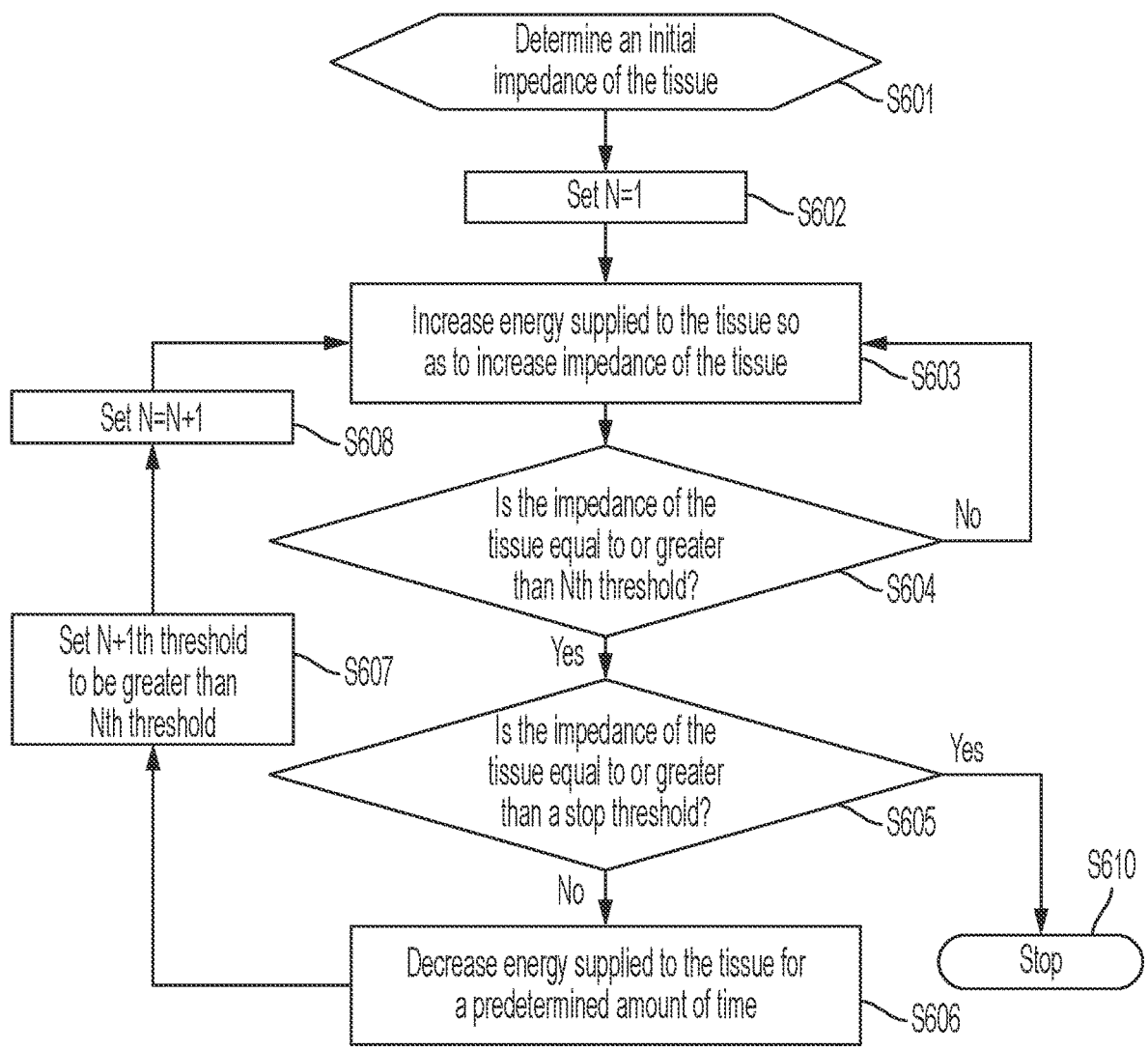
FIG. 6 illustrates a flow chart for an alternate method of sealing a living tissue in accordance with some embodiments.

FIG. 6 illustrates a flow chart for an alternate method of sealing a living tissue in accordance with some embodiments. The process illustrated in FIG. 6 differs from the process illustrated in FIG. 4 in that the energy supplied to the tissue in FIG. 6 is decreased for a predetermined amount of time rather than until the impedance is decreased by a predetermined value as in FIG. 4. Accordingly, only the differences in the two processes are described in detail herein to avoid duplication.

For example, the process illustrated in FIG. 6 is identical to the process illustrated in FIG. 4 until S605. However, in the process illustrated in FIG. 6, at S606, the electrical energy supplied to the tissue is decreased by a certain value and/or for a certain amount of time. For example, the electrical energy supplied to the tissue may be reduced to zero and/or to a low value that cannot affect the tissue being treated, e.g., by reducing the voltage across the tissue to zero for a certain amount of time such as for 10 ms, 15 ms, 20 ms, 30 ms, 35 ms, 40 ms, 50 ms, 60 ms, 70 ms, 80 ms, 90 ms, 100 ms, 125 ms, 150 ms, 200 ms, or any amount of time between any two of these values.

Once the electrical energy supplied to the tissue is decreased for the predetermined amount of time, at S607, the threshold impedance for the subsequent cycle, i.e., N+1-th threshold, is set to be higher than that of the current cycle (i.e., the Nth cycle). The N+1-th threshold may be set to be greater by a certain predetermined value in some embodiments. The predetermined value by which the N+1-th threshold is greater than the Nth threshold may be based on the size of the tissue and/or the type of the tissue in some embodiments.

The cycle counter is then set, at S608, to N+1 (i.e., N=N+1), after which the process continues at S603.

The system and method disclosed herein reduce the time required for sealing a living tissue during an electrosurgical procedure. The system and method disclosed herein further reduce the incidence of overheating the tissue, thereby improving patient safety. In addition, by controlling the rate of rise in impedance of the living tissue, the system and method disclosed herein improves the efficiency of the process of sealing the living tissue.

Although the present invention has been described in connection with the above exemplary embodiments, it will be appreciated by those skilled in the art that additions, deletions, modifications, and substitutions not specifically described may be made without department from the spirit and scope of the invention as defined in the appended claims.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The singular forms "a," "an," and "the" include plural referents unless the context clearly dictates otherwise. Thus, for example, reference to "a plunger component" includes reference to one or more plunger components, and reference to "the magnet" includes reference to one or more magnets.

In one or more aspects, the terms "about," "substantially," and "approximately" may provide an industry-accepted tolerance for their corresponding terms and/or relativity between items, such as from less than one percent to five percent.

As used herein, the term "substantially" refers to the complete or nearly complete extent or degree of an action, characteristic, property, state, structure, item, or result.

It is to be understood that a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.5 to 10 cm" should be interpreted to include not only the explicitly recited values of about 0.5 cm to about 10.0 cm, but also include individual values and sub-ranges within the indicated range. Thus, included in this numerical range are individual values such as 2, 5, and 7, and sub-ranges such as from 2 to 8, 4 to 6, etc. This same principle applies to ranges reciting only one numerical value. Furthermore, such an interpretation should apply regardless of the breadth of the range or the characteristics being described.

Unless otherwise defined, all technical and scientific terms used herein have the same meaning as commonly understood to one of ordinary skill in the art to which this disclosure belongs. Although any methods, devices and materials similar or equivalent to those described herein can be used in the practice or testing of the disclosure, representative methods, devices, and materials are described below.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

The techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, performs one or more of the methods described above.

The non-transitory processor-readable storage medium may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor. For example, a carrier wave may be employed to carry computer-readable electronic data such as those used in transmitting and receiving electronic mail or in accessing a network such as the Internet or a local area network (LAN). Many modifications may be made to this configuration without departing from the scope or spirit of the claimed subject matter.

Although the detailed description contains many specifics, these should not be construed as limiting the scope of the subject technology but merely as illustrating different examples and aspects of the subject technology. It should be appreciated that the scope of the subject technology includes some embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A method for sealing a living tissue using high frequency electrical energy, the method comprising:

applying an amount of high frequency electrical energy to the living tissue in at least two cycles, wherein the at least two cycles include a N-th cycle and a N+1-th cycle following the N-th cycle, wherein, during the N-th cycle, the applying includes:

increasing an amount of the high frequency electrical energy until an impedance of the living tissue reaches an N-th impedance threshold value, and when the impedance reaches the N-th impedance threshold value, decreasing the amount of the high frequency electrical energy, and wherein, during the N+1-th cycle, the applying includes:

increasing the amount of the high frequency electrical energy until the impedance of the living tissue reaches an N+1-th impedance threshold value that is greater than the N-th impedance threshold value, and wherein, when N=1, the N-th cycle of the method further comprises:

determining a size parameter associated with the living tissue by applying a constant power to an end effector of a treatment instrument for a predetermined period of time while the end effector is in contact with the living tissue, where determining the size parameter occurs prior to increasing the amount of the high frequency electrical energy in the N-th cycle.

2. The method of claim 1, further comprising:

during the N+1-th cycle, when the impedance reaches the N+1-th impedance threshold value, decreasing the amount of the high frequency electrical energy.

3. The method of claim 1, wherein the N+1-th impedance threshold value is an N+1-th impedance stop value, and the method further comprises:

during the N+1-th cycle, when the impedance reaches an N+1-th impedance stop value, stopping the application of high frequency electrical energy to the living tissue.

4. The method of claim 1, further comprising determining a value of N based on the size parameter.

5. The method of claim 1, further comprising estimating the N-th impedance threshold value based on the size parameter.

6. The method of claim 1, wherein a rate of increase of the high frequency electrical energy in the N+1-th cycle is different from a rate of increase of the high frequency electrical energy in the N-th cycle.

7. The method of claim 1, wherein the N+1-th cycle of the method further comprises:
determining an N+1-th size parameter associated with the living tissue by applying a constant power to the end effector for a predetermined period of time while the end effector is in contact with the living tissue, where determining the N+1-th size parameter occurs prior to increasing the amount of the high frequency electrical energy in the N+1-th cycle.

8. The method of claim 7, wherein a rate of increase of the high frequency electrical energy in the N+1-th cycle is determined based on the N+1-th size parameter.

9. The method of claim 8, wherein the rate of increase of the high frequency electrical energy in the N+1-th cycle is different from a rate of increase of the high frequency electrical energy in the N-th cycle.

10. A device for sealing a living tissue, the device comprising:
an energy source configured to generate high frequency electrical energy;
an end effector configured to connect to the energy source and configured to provide the high frequency electrical energy to the living tissue; and
a controller configured to apply an amount of the high frequency electrical energy to the living tissue in at least two cycles,
wherein the at least two cycles include a N-th cycle and a N+1-th cycle following the N-th cycle,
wherein, in the N-th cycle, the controller is further configured to:
increase the amount of the high frequency electrical energy until an impedance of the living tissue reaches an N-th impedance threshold value, and
when the impedance reaches the N-th impedance threshold value, decrease the amount of the high frequency electrical energy, and
wherein, in the N+1-th cycle, the controller is further configured to:
increase the amount of the high frequency electrical energy until the impedance reaches an N+1-th impedance threshold value that is greater than the N-th impedance threshold value, and
wherein, when N=1, in the N-th cycle, the controller is further configured to:
determine a size parameter associated with the living tissue by applying a constant power to the end effector for a predetermined period of time while the end effector is in contact with the living tissue, where determining the size parameter occurs prior to increasing the amount of the high frequency electrical energy in the N-th cycle.

11. The device of claim 10, wherein, in the N+1-th cycle, the controller is further configured to decrease the amount of the high frequency electrical energy when the impedance reaches the N+1-th impedance threshold value.

12. The device of claim 10, wherein the N+1-th impedance threshold value is an N+1-th impedance stop value, and,
wherein, in the N+1-th cycle, the controller is further configured to stop the application of high frequency electrical energy when the impedance reaches the N+1-th impedance stop value.

13. The device of claim 11, wherein the controller is further configured to determine a value of N based on the size parameter.

14. The device of claim 11, wherein the controller is further configured to estimate the N-th impedance threshold value based on the size parameter.

15. The device of claim 11, wherein a rate of increase of the high frequency electrical energy in the N+1-th cycle is different from a rate of increase of the high frequency electrical energy in the N-th cycle.

16. The device of claim 11, wherein, in the N-th cycle, the controller is further configured to determine an N+1-th size parameter by applying a constant power to the end effector for a predetermined period of time while the end effector is in contact with the living tissue, and
wherein the N+1-th size parameter is determined prior to increasing the amount of the high frequency electrical energy in the N+1-th cycle.

17. The device of claim 16, wherein a rate of increase of the high frequency electrical energy in the N+1-th cycle is determined based on the N+1-th size parameter.

18. The device of claim 17, wherein the rate of increase of the high frequency electrical energy in the N+1-th cycle is different from a rate of increase of the high frequency electrical energy in the N-th cycle.

* * * * *